United States Patent [19]

Speiser

[11] Patent Number: 4,880,634

[45] Date of Patent: Nov. 14, 1989

[54] LIPID NANO-PELLETS AS EXCIPIENT SYSTEM FOR PERORALLY ADMINISTERED DRUGS

[75] Inventor: Peter Speiser, Zurich, Switzerland

[73] Assignee: Dr. Rentschler Arzneimittel GmbH & Co., Laupheim, Fed. Rep. of Germany

[21] Appl. No.: 66,459

[22] Filed: Jun. 26, 1987

Related U.S. Application Data

[63] Continuation of Ser. No. 740,771, Jun. 30, 1985, abandoned.

[30] Foreign Application Priority Data

Jun. 8, 1984 [DE] Fed. Rep. of Germany ....... 3421468

[51] Int. Cl.$^4$ ...................... A61K 37/22; A61K 9/50; A61K 47/00
[52] U.S. Cl. .................................. 424/450; 424/502; 514/786
[58] Field of Search ............... 514/786, 943, 938, 937, 514/964; 424/502, 450

[56] References Cited

U.S. PATENT DOCUMENTS

| | | | |
|---|---|---|---|
| 4,115,313 | 9/1978 | Lyon et al. | 252/309 |
| 4,331,654 | 5/1982 | Morris | 424/450 |
| 4,356,167 | 10/1982 | Kelly | 424/450 |
| 4,372,949 | 2/1983 | Kodama et al. | 504/78 |

FOREIGN PATENT DOCUMENTS 3421468 12/1985 Fed. Rep. of Germany .
8300294 of 1983 PCT Int'l Appl. .

OTHER PUBLICATIONS

Chemical Abstracts 80,52392a (1974).

*Primary Examiner*—Jerome D. Goldberg
*Assistant Examiner*—Raymond J. Henley, III
*Attorney, Agent, or Firm*—James W. Hellwege

[57] ABSTRACT

An excipient system containing a drug for peroral administration in the form of an ultrafine aqueous, colloidal suspension of lipid nano-pellets comprised of lipids and a surfactant of which the particle diameters of the nano-pellets range from 50–1,000 nm, preferably from 80–800 nm, the ratio of lipid to surfactant in the lipid nano-pellets ranging from 1:0.1 to 1:2.2, preferably from 1:0.22 to 1:1.2, especially from 1:1 to 1:0.22, and where the lipid nano-pellets are present in the suspension in a concentration of from 1–20% by weight. The lipid nano-pellets can be provided with pharmacologically active substances, making possible improved biological availability upon peroral administration.

28 Claims, No Drawings

LIPID NANO-PELLETS AS EXCIPIENT SYSTEM FOR PERORALLY ADMINISTERED DRUGS

CROSS-REFERENCE TO RELATED APPLICATIONS

This application is a continuation of application Ser. No. 740,771, filed June, 3, 1985, now abandoned.

BACKGROUND OF THE PRESENT INVENTION

The present invention is directed to lipid nano-pellets with an average particle size of 50 to 1,000 nm, preferably 80 to 800 nm, which can be used as the excipient system for drugs and which are well suited for peroral administration.

Drugs of biologically active substances which are to be applied in a targeted manner at specific sites in a living organism and which avoid rapid elimination comprise a formulation wherein an active substance is bound to specific excipients or enclosed thereby, such that there shall be no premature release of the substance. Following administration, the release of the effective substances as a rule takes place in the gastro-intestinal tract, the drug either breaking up into particles and the effective substance being dissolved by the digestive liquid, or else the effective substance is only dissolved from the intact initial form by diffusion. This process may take place rapidly or delayed in time (retardation). In all cases, the effective substance after the ensuing resorption passes through the liver (first pass effect) where it is metabolized in part or whole, that is, where it is chemically converted and therefore arrives at the target site only in part.

Long ago small particles were developed for the retarded release of effective substances which substances are enclosed therein. The accessory materials required to fabricate such particles, however, are often physiologically unacceptable, or else the manufacturing methods are costly, or again the particle stability is low. Administered perorally, the effective substance is either dissolved from the particle by diffusion in the digestive tract, or it is released by the enzymatic decay of the particle skin. In both cases, however, the resorbed active substance will then again be subjected to the first pass effect in the liver. Such small particles include micro-capsules, nano-capsules and liposomes.

As a rule, microcapsules made from gelatins or cellulose derivatives incur the drawback that a costly method is required for production and that their particle size is in the micron range.

Nano-capsules as a rule are prepared from polyacryl-amides and polycyanoacrylates and other synthetic raw materials. These suffer from the drawback of evincing some toxicity and therefore often are unsuitable for human application.

Liposomes are highly ordered phospholipid-based structures of one or more lipid double layers forming a membrane into the gaps of which substances of proper size will be included. Their size depends on the liposomes being multilaminar or smaller, monolaminar types. The liposomes suffer from the drawback that they are rather unstable.

Volkheimer (*Adv. in Pharmacol. Chemoth.* 14 [1977] pp. 163-187) has shown by means of starch grains that small, solid particles from the intestine can be found unchanged in the blood and urine. This transport phenomenon, termed "persorption", of intact particles through the intestinal wall however is substantially incomplete. Volkheimer assumes that only 1 of 50,000 of the persorbable particles actually is persorbed. In the case of starch this is not surprising because the starch grains have particle diameters for instance of 2 to 10 microns as regards rice starch and 10 to 25 microns for maize starch. Besides, starch evinces strongly hydrophilic properties whereas preferably lipophilic substances are absorbed in the intestine.

It is furthermore known that long-chain fatty acids with chain lengths of more than 12 carbon atoms are routed not to the liver, but preferably to the lymph system and that by means of a special persorption process, called endocytosis, small droplets or solid particles can pass through the intestinal wall and thereupon are routed into the lymph flow.

The object of the invention is thus to provide drug-carrying particles which are small enough to be persorbed and which are adequately lipophilic and physiologically compatible in order to transport the drug they contain in widely unchanged form through the intestine wall. As a result there is achieved an improvement in the availability at the site of action (resorption improvement) for such effective active drug substances which are poorly resorbed in the known perorally administered forms since they are either poorly soluble, not adequately or at all resorbed in the digestive tract, metabolized too rapidly, metabolized too much, or because they are already destroyed by enzymatic or chemical factors in the digestive tract. Such particles should also preferably be solid at room temperature.

In U.S. Pat. No. 4,331,654 (or the corresponding European patent application No. 0042249) a description exists of magnetically detectable, biodegrading water-free drug carrier consisting of lipid particles as excipients for effective substances, which particles are used in intra-arterial injection and have sizes less than 5,000 nm, preferably of an average size of from 1,000–2,000 nm, and which furthermore contain one or more non-toxic surfactants. The lipids used are fatty acids with melting points between 30° and 100° C., in particular saturated fatty acids, alcohols of higher molecular weights, mono-, di- and tri-glyceride inclusive, glycerin esters of the fatty acids, phospholipids, sterols and cerobrosides. The lipid particles melt above 30° C. The cited surfactants are both ionic and non-ionic, such as polyoxyethylenesorbitane monooleate, salts of long-chain aliphatic alcohols, quaternary ammonium salts and lecithin. Inorganic magnetite, which is insoluble in the lipid phase, is used as the magnetically-responsive substance, the particles being prepared by producing a dispersion in water above the lipid melting point, and isolating the solid micro-particles by lyophilization after cooling. A drug substance may be incorporated into the dispersion.

SUMMARY OF THE INVENTION

In accordance with the present invention there is thus provided an excipient system containing a pharmacologically active substance for peroral administration characterized in that the excipient system comprises lipid nano-pellets having a particle size of from about 50 to 1,000 nm in the form of an aqueous, colloidal suspension, the lipid particles being present in the suspension in a concentration of from about 1 to 20% by weight, said lipid particles comprising a mixture of at least one lipid and at least one surfactant in a ratio of from about 1:0.1 to 1:2.2, respectively, said particles comprising from about 5 to 70% by weight of at least one lipid, from about 0.0) to 70% by weight of at least one surfactant, and from about 0.05 to 25% by weight of a pharmacologically active substance.

In accordance with another aspect of the present invention there is provided a method of production of an excipient system containing a pharmacologically active substance for peroral administration comprised of lipid nano-pellets having a particle size of from about 50 to 1,000 nm in the form of an aqueous, colloidal suspension, the lipid particles being present in the suspension in a concentration of from about 1 to 20% by weight, said lipid particles comprising a mixture of at least one lipid and at least one surfactant in a ratio of from about 1:0.1 to 1:2.2, respectively, said particles comprising from about 5 to 70% by weight of at least one lipid, from about 0.01 to 70% by weight of at least one surfactant, and from about 0.05 to 25% by weight of a pharmacologically active substance, said method comprising forming an admixture of said at least one surfactant and said pharmacologically active substance with said at least one lipid with said lipid being caused to be in the form of a melt, dispersing said admixture within an aqueous solution maintained at a temperature above the melting point of said lipid and under dispersing conditions sufficient to produce lipid nano-pellets of a particle size of from about 50 to 1,000 nm upon the thus-formed suspension being caused to cool below the melting point of said lipid.

In accordance with the present invention there is further provided an excipient system containing a pharmacologically effective substance for peroral administration characterized in that the excipient system comprises lipid nano-pellets having a particle size of from about 50 to 1000 nm, said lipid particles comprising a mixture of at least one lipid and at least one surfactant in a ratio of from about 1:0.1 to 1:2.2, respectively, said particles comprising from about 5 to 70% by weight of at least one lipid, from about 0.01 to 70% by weight of at least one surfactant, and from about 0.05 to 25% by weight of an effective substance.

DETAILED DESCRIPTION OF THE INVENTION

The present invention is directed to an excipient system consisting of an ultrafine colloidal suspension of nano-pellets of lipids and of surfactants, the diameters of the colloidal particles (nano-pellets) ranging from about 50 to 1,000 nm, in particular, ranging from about 80 to 800 nm.

The pharmacologically effective substance introduced into the excipient system are thoroughly dissolved in the lipids during the preparation of the lipid nano-pellets, though they may also be present in crystalline form or amorphously or as mixtures of such crystallographic states when the effective substances crystallize out or are precipitated following cooling to room temperature.

The effective substance may be directly introduced into the lipid by various methods such as into the molten lipid or lipid mixture or in a molten mixture of lipid and surfactant, or by integrating the surfactant and the effective substance into an organic, volatile solvent such as a chlorinated hydrocarbon (e.g., chloroform, carbon tetrachloride, methylene chloride) or alcohols (e.g., ethanol) and by introducing this solution into the molten lipid. Following careful admixture or dissolution while stirring or agitating, the volatile solvent is then be removed by evaporation.

A variety of biodegradable lipids may be employed in the present invention. Lipids such as mono-, di- and tri-glycerides of saturated, straight-chain fatty acids with 12 to 30 carbon atoms such as lauric acid, myristic acid, palmitic acid, stearic acid, arachidic acid, behenic acid, lignoceric acid, cerotinic acid, melissic acid, as well as their esters of other polyvalent alcohols such as ethylene glycol, propylene glycol, mannitol, sorbitol, saturated fatty acids with 12–22 carbon atoms such as lauryl alcohol, myristyl alcohol, cetyl alcohol, stearyl alcohol, arachidyl alcohol, behenyl alcohol, saturated wax alcohols with 24–30 carbon atoms such as lignoceryl alcohol, ceryl alcohol, cerotyl alcohol, myricyl alcohol, are used. Animal and plant phospholipids such as lecithin and their hydrogenated forms, and polypeptides such as gelatins along with their modified forms can be used. The various lipids can be used alone or in admixture.

The lipids employed preferably exhibit a melting point in the range of from about 30° to 100° C.

A wide variety of non-toxic surfactants can be employed in the present invention. The physiological bile salts such as sodium cholate, sodium dehydrocholate, sodium deoxycholate, sodium glydocholate, sodium taurocholate etc. are preferably employed as physiologically acceptable surfactants.

Suitable synthetic surfactants are the salts of the sulfosuccinic acid esters, polyoxyethylenesorbitane esters, sorbitane esters and sorbitane ethers, polyoxyethylene fatty alcohol ethers, polyoxyethylene stearic acid esters and also corresponding mixed condensates of polyoxyethylene ethers and polyoxypropylene ethers (e.g., Pluronics®), ethoxylated saturated glycerides, (e.g., Labrafile®) and partial fatty acid glycerides and polyglycides (e.g., Gelucire®).

Various pharmacologically effective substances may be employed in the excipient system comprised of the lipid and surfactant. Suitable effective substances are those which evince poor bioavailability (i.e., which dissolve poorly), which either are not at all or not adequately resorbed in the digestive tract or are metabolized too rapidly or too much, or which are destroyed in the digestive tract by enzymatic or chemical activity.

Especially suitable effective substances for use in the present invention are identified below:
1. Insulins, such as
natural, semi-synthetic, synthetic insulins
proinsulin
2. Antidiabetics, such as
glipizide
gliclazid
ciglitazone
3. Vitamins, such as
vitamin A
vitamin B
4. Anticoagulants such as
heparin
Gabexat-Mesilat
5. Fibrinolytics such as
urokinase
plasminogenic activator
6. Antithrombotics such as
Suloctidil
Nafazatrom
Picotamid
heparin oligosaccharides
Antithrombin III
7. Lipid-lowering agents such as Beclobrat
Bezafibrat
Etofibrat
Fenofibrat
8. Blood fractions such as
albumins
antithrombins
Factor IX
Factor VIII
haptoglobulin
9. Cardiac glycosides such as
digitoxin
digoxin
methyl digoxin
acetyl digoxin
K-strophanthin
10. Vasodilators such as
Molsidomin
Hydralazine
Dihydralazine
Nicorandil
11. Calcium antagonists such as
Diltiazem
Flunarizin
Gallopamil
Verapamil
Nifedipine
Nicardipin
Nimodipine
Nitrendipin
Lidoflazin
Niludipin
12. ACE inhibitors such as
Captopril
Enlapril
SA-466
13. Antihypertension agents such as
Minoxidil
Dihydroergotoxin
Dihydroergotoxin-Mesilat
Endralazin
14. Alpha+beta blockers such as
Labetalol
Sulfinalol
Bucindolol
15. Diuretics such as
Triamterene
Hydrochlorothiazide
Furosemid
Piretanid
Metolazone
16. Peripherally effective vasodilators such as
Buflomedil
Minoxidil
Cadralazin
Propentofyllin
17. Antihypotensive agents such as
Dihydroergotamin
Dihydroergotamin-Mesilate
Gepefrin
18. Beta blockers such as
Talinolol
Propanolol
Atenolol
Metoprolol
Nadolol
Pindolol
Oxprenolol
Labetalol
19. Systemically acting antimicotics such as
Ketoconazol
Griseofulvin
20. Contraceptives such as
Binovum
Desogestrel
Triquilar
21. Steroid hormones such as
Testosterone
Testosterone undecanoate
Progesterone
Pregnenolone
Corticosterone
Cortisol
Cortisone
Prednisone
Prednisolone
Methylprednisolone
Dexamethasone
22. Prostaglandins, Prostacyclins such as
Alprostadil
Carboprost
Epoprostenol
Sulproston
23. Lactation inhibitors such as
Bromocryptine
Metergoline
24. Growth hormones such as
Somatropin
25. Somatostatin such as
Stilamin
Somastotine and its derivatives
26. Cephalosporins such as
Cefamandol
Cefmenoxim
Cefoperazon
Ceftizoxim
Cefalexin
Cefalotin
Cefazedon
Cefotaxim
Cefoxitin
Cefsulodin
27. Antibiotics such as
Fosfomycin
Fosmidomycin
Rifapentin
28. Antiviral agents such as
Aciclovir
Metisoprenol
Tromantadine
Vidarabine
Vidarabine-Na-Phosphate
Immuno-globulin
29. Interferons, Lymphoquins such as
alpha interferon
beta interferon
gamma interferon
30. Vaccines, such as
Corynebateria parrum
Hepatitis B vaccine
Lactobacillus vaccine
Pneumococcal vaccine
31. Cytostatics such as
Chloromethine
Cyclophosphamide
Melphalan Chlorambucil
Busulfan
Thio-TEPA
Methotrexate
5-Flururacil
Cytarabine
6-Mercaptopurine
Vincristine
Vinblastine
Vindesin
Actinomycin D
Mytomycin C
Mytramycin
Doxorubicin
Belomycin
Cisplatin
Procarbacin
Estramustine
Thioguanine
32. Radio diagnostic means such as
Aminofostin
Misonidazol
33. Antirheumatic means such as
Indometacin
Diclofenac
Ibuprofen
Ibuproxam
Ketoprofen
Pirprofen
Suprofen
34. Antimigraine means such as
Clonidine
Flunarizin
Metergoline
Nadolol
Dopamine antagonists
35. Enkephalins such as
Metkephamide
beta endorphin
enkephalin
36. Antiparkinson means such as
Memantin
Piribedil
Mesulergin
Desocryptin
Lisuride hydrogen maleate
37. Cerebrally acting vasodilators such as
Dihydroergotoxin
Dihydroergooxin-Mesilate
Ciclonicate
Vinburin
Vinpocetin
Vincamine
38. Bronchospamolytics such as
Ipratropium bromide
Chromoglycinic acid
Sobrerol
39. Antiallergics such as
Ketotifen fumarate
Procaterol
Tiaramide
Tranilast
40. Hypnotic means, sedatives such as
Flurazepam
Nitrazepam
Lorazepam
41. Psycho-pharmaceuticals such as
Oxazepam
Diazepam
Bromazepam The lipid nano-pellets or particles of the present invention are solid at room temperature and have the following composition:
  5 to 70% by weight of a lipid or mixture of lipids;
  0.01 to 70% by weight of a surfactant or mixture of surfactants; and
  0.05 to 25% by weight of an effective substance.
Furthermore, other additives that might favorably affect the preparation of the lipid nano-pellets such as peptizers and dispersion agents may be included.

The ratio of the lipid to the surfactant ranges from about 1:0.01 to 1:2.2 and preferably from about 1:0.22 to 1:1.2. Ratios of from about 1:1 to 1:0.22 (lipid:surfactant) are especially preferred.

The lipid nano-pellets of the present invention can be prepared by initially melting the lipid or lipid mixture. Simultaneously, distilled water is heated to approximatley the same temperature, which is above the melting point of the lipid and generally in the range of from about 30 to less than 100° C. (e.g., from about 70° to 85° C.). Depending upon their physical characteristics, the surfactant may be dissolved or dispersed either in the molten lipid or in the water. The pharmacologically effective substance may be added to the lipid in molten form or dissolved or dispersed in the molten lipid. It is also possible for the introduction of such substances to be implemented by means of a solvent and evaporating the solvent subsequent to addition to the molten lipid. The warm, aqueous phase is subsequently added to the molten lipid and thoroughly admixed therewith, sufficiently dispersed (e.g., in a stirrer of high angular speed), and cooled to below the melting point of the lipid or to room temperature under strring. The lipid employed will preferably melt at a temperature above room temperature to facilitate use of the excipient product. As a rule the dispersal step (e.g., the treatment with a high angular speed agitator followed by ultrasonic treatment at suitable frequencies and time intervals) is carried out until the desired lipid particle size of about 50 to 1,000 nm is attained. The aqueous suspension comprises the lipid particles in a concentration of from about 1 to 20% by weight, preferably from about 8 to 15% by weight. A concentration of about 10% by weight is especially preferred.

An aqueous suspension of lipid nano-pellets is thus formed which pellets exhibit a particle size between about 50 and 1,000 nm. This suspension has a suitably long shelf-life and can be used directly for its application. When administered perorally, this suspension is used in a manner consistent with the type of effective substance present, the amount of effective substance present and the therapeutic dose which is commonplace for such administration.

However, it is also possible to separate the nano-pellets from the suspension using methods known per se, or to enrich them. By way of illustration, following ultra-centrifuging and ensuing lyophilization, one obtains a powder representing a further stable form. The dry lyophilisate as such can be divided into therapeutic doses (e.g., in the form of a powder, tablets, capsules) and be administered as such.

The advantage of the lipid nano-pellets of the invention is the physiological composition of the excipient system and the simple method of production thereof. An important advantage is that due to the lipophilic nature of the lipid nano-pellets of the invention and their small size of between about 50 and 1,000 nm, preferably from about 80 to 800 nm, the pellets can be persorbed in the digestive tract through the intestinal wall and the intact lipid excipient together with the pharmacologically effective substance can accordingly enter the body tissue while circumventing the first pass effect through the liver. This mechanism of fat absorption provides a good distribution of the effective substance in the tissue. The lipid particles of the invention are stored in the fat tissue and thereby provide a deposition effect for the effective substance. Due to the enzymatic fat decay, the effective substance is released over a longer period of time than possible heretofore with the conventionally orally administered types of pharmacologically effective substances (in particular the retarded ones) because the release of conventional substances is restricted by the average 8 hour dwell time of the drug in the digestive tract.

Again, advantageously, the achieved deposition effect from the lipid nano-pellets of the invention restricts the ingestion of the drug at most to once daily, contrary to conventional substances (including the retarding forms), which are administered several times a day. This assures improved therapeutical reliability.

The invention is additionally illustrated in connection with the following Examples which are to be considered as illustrative of the present invention. It should be understood, however, that the invention is not limited to the specific details of the Examples.

EXAMPLE 1

3 g of tristearin are melted in a dissolving glass (3.5 cm in diameter, 20 cm long) in an 85° C. water-bath. 0.3 g of gelatin are allowed to swell in 54.9 g of distilled water for 15 minutes at room temperature and then are dissolved with careful heating and agitation in the water-bath. This solution is kept another 15 minutes at a constant temperature of 85° C. 1.8 g of egg lecithin are dispersed in the molten tristearin. The gelatin solution thermostated at 85° C. is added to the molten fat phase and the whole mixture is shaken for 10 seconds and dispersed for 1.5 minutes in a commercial agitator at 20,000 rpm. This is followed by cooling to room temperature with slight stirring. An ultrafine suspension of the lipid particles with a size of about 1,000 nm is obtained, the concentration of the suspension being 8.5% by weight. The ratio of lipid to surfactant is 1:0.7.

EXAMPLE 2

3 g of tristearin are melted in a dissolving glass in a waterbath at 85° C. 1.2 g of Tween 80 and 2.4 g of Span 80 are added to this melt. 53.4 g of distilled water at 85° C. are added to the fat phase and the admixture dispersed and cooled as in Example 1, thereby providing a stable suspension of which the lipid particles have a size of about 100 to 350 nm. The suspension concentration is 12.4% by weight. The ratio of lipid to surfactant is 1:1.2.

EXAMPLE 3

3 g of tristearin are melted in a dissolving glass in a water bath at 85° C. 0.06 g of sodium cholate are dissolved in 56.34 g of distilled water thermostated at 85° C. 0.06 g of phospholipone 100-H (hydrogenated lecithin) are dissolved in 4 ml of chloroform and added to the molten tristearin and twice rinsed with 2 ml of chloroform. The chloroform is removed over a period of 15 minutes at 85° C. with agitation. Then the mixture is dispersed as in Example 1 and cooled. The particle size of the lipid particles of the obtained suspension is about 1,000 nm. The concentration of the suspension is 6.1% by weight, with the ratio of lipid to surfactant being 1:0.22.

EXAMPLE 4

2 g of tristearin are melted in a 300 ml Erlenmayer flask at 85° C. 0.04 g of sodium cholate are dissolved in 200 ml of distilled water in a 300 ml Erlenmayer flask and heated to 85° C. 0.4 g of Phospholipon 100 H are dissolved in 4 ml of chloroform and added to the molten tristearin. This is followed with dual after-rinsing each time with 2 ml of chloroform. The chloroform is removed over a period of time of 15 minutes at 85° C. The hot water phase is added to the fat phase and is shaken by hand for 10 seconds, whereupon dispersion is implemented for 1.5 minutes in a 20,000 rpm stirrer followed by 20 minutes of ultrasonic treatment at about 20 kHz with an ultrasonic type apparatus. Thereupon the mixture is cooled to room temperature with slight agitation by a magnetic stirrer. The particle size of the suspension is about 100 nm on the average as measured along the longest visible part of the particle. The concentration of the suspension is 1.2% by weight, the ratio of lipid to surfactant being 1:0.22.

EXAMPLE 5

6 g of tristearin are melted at 85° C. as indicated in Example 4. 4 g of low-fat milk are dispersed in 200 ml of distilled water in a 200 ml Erlenmeyer flask thermostated at 85° C. 2 g of Phospholipon 100 H are dissolved in 5 ml of chloroform and added to the molten tristearin and after-rinsed twice with 2 ml of chloroform each time. The suspension is prepared by the procedure of Example 4. The particle size is about 100-400 nm. The suspension concentration is about 4% by weight, with the ratio of lipid to surfactant being about 1:0.3.

EXAMPLE 6

10 g of propylene glycol distearate are melted at 85° C. as in Example 4. 0.2 g of sodium cholate are dissolved as in Example 4 in distilled water thermostated at 85° C. 2 g of Phospholipon 100 H are dissolved in 5 ml of chloroform and added to the molten propylene glycol distearate and thereupon, as stated in Example 4, the suspension is prepared. The particle size is about 100 nm. The concentration of the suspension is about 5.8% by weight, with the ratio of lipid to surfactant being 1:0.22.

EXAMPLE 7

0.6 g of testosterone undecanoate are melted together with 2 g of tristearin in a water bath at 85° C. Thereupon, and in the same manner as in Example 4, the procedure to prepare the suspension is followed. The particle size of the lipid particles containing the effective substance is about 50–60 nm. The concentration of the suspension is about 1.5% by weight, the ratio of the lipid to surfactant being 1:0.22. The proportion of effective substance in the lipid nano-pellet is 19.7%.

EXAMPLE 8

2 g of octadecanol (stearyl alcohol) and 0.6 g of testosterone undecanoate are melted at 85° C. as in Example 4 and, as stated in Example 4, the suspension of the lipid particles is prepared. The particle size is on the average 100 nm. The concentration of the suspension is about 1.5% by weight, with the ratio of the lipid to the surfactant being 1:0.22. The proportion of effective substance in the lipid nano-pellets is 19.7%.

EXAMPLE 9

2.0 g of polyethyleneglycol sorbitane monooleate (Tween 80) are placed in a glass beaker, then 0.2 g of Beclobrat are added and dissolved with stirring and heating to about 70° C. 20 g of stearyl alcohol are melted in a separate beaker. Both melts are combined under stirring. A clear solution is obtained. 178 g of water are placed in a 500 ml Erlenmeyer flask and heated to 70° C. The lipid phase is stirred into the water and then the mixture is dispersed for 5 minutes by means of ultrasonic treatment at 35 kHz. This is followed by cooling to room temperature with slight stirring. The suspension so obtained is diluted with an additional 100 g of water. The size of the lipid particles is about 800 nm. The concentration of the suspension is 7.4% by weight. The ratio of lipid to surfactant is 1:0.1. The effective substance is 0.9% of the lipid nano-pellets.

EXAMPLE 10

2.0 g of polyethyleneglycol sorbitane monooletate (Tween 80) are heated to 70° C. Into this substance are stirred 0.2 g of Molsidomin. 20 g of stearyl alcohol are heated and melted in a separate vessel. The lipid is stirred into the solution containing the effective substance. A clear solution is obtained. 178 g of water are placed into a 500 ml Erlenmeyer flask and heated to 70° C. The lipid phase containing the effective substance is stirred into the water and then is treated for 20 minutes with ultrasonics of about 35 kHz. This is followed by cooling to room temperature. The particle size of the suspension so obtained is about 500 nm. The concentration of the suspension is 11.1% by weight, with the ratio of lipid to surfactant being 1:0.1. The proportion of effective substance in the lipid nanopellets is 0.9% by weight.

EXAMPLE 11

2.0 g of polyethylene glycol sorbitan monostearate (Tween 60) are heated in a glass beaker to 70° C. 0.2 g of Nifedipin are dissolved therein with stirring. 20.0 g of stearyl alcohol are heated to 70° C. in a separate glass beaker. The lipid is added with stirring to the mixture containing the effective substance. A clear solution is obtained. 178 g of water are placed in a 500 ml Erlenmeyer flask and heated to 70° C. The lipid phase is stirred into the water and dispersed ultrasonically at 35 kHz for 5 minutes. Thereupon cooling to room temperature takes place in the presence of slight stirring. The size of the particles of the lipid nano-pellets is about 800 nm. The concentration of the suspension is 11.1% by weight. The ratio of lipid to surfactant is 1:0.1. The proportion of the effective substance in the lipid nano-pellets is 0.9% by weight.

EXAMPLE 12

2.25 g of polyethyleneglycol sorbitane monooleate (Tween 80) are heated to 70° C. Into this substance are dispersed 0.15 g of Vincamine. 22.5 g of stearyl alcohol also are preheated to 70° C. and added to the solution containing the effective substance. A clear solution is obtained. 178 g of water are placed in a 500 ml Erlenmeyer flask and heated to 70° C. The lipid phase containing the effective substance is stirred therein and the mixture is dispersed ultrasonically at 35 kHz for 15 minutes. This is followed by cooling to room temperature with slight stirring. Thereupon the suspension is diluted with 100 g of ice water. The particle size of the suspension is about 400 nm. The concentration of the suspension is 8.2% by weight. The proportion of the effective substance in the lipid nano-pellets is 0.6% by weight.

EXAMPLE 13

2.0 g of polyethyleneglycol sorbitane monostearate (Tween 60) are heated to 70° C. 0.4 g of Flurazepam are dispersed therein. 20 g of stearyl alcohol which were separately preheated to 70° C. are added to that dispersion. A clear solution is obtained. 178 g of water are placed in a 500 ml Erlenmeyer flask and are heated to 70° C. The lipid phase containing the effective substance is added with stirring to this water. This is followed by dispersing for 7 minutes using ultrasonics of about 35 kHz. Next the mixture is cooled with agitation by a magnetic stirrer to room temperature. The size of the lipid nano-pellets so obtained is about 900 nm. The concentration of the suspension is 11.2% by weight, with the ratio of lipid to surfactant being 1:0.1. The proportion of effective substance in the lipid nano-pellets is 1.8% by weight.

EXAMPLE 14

20.0 g of stearyl alcohol are heated to 70° C. 2.0 g of soy bean lecithin and 0.6 g of Indometacin are stirred into that melt. A clear mixture is obtained. 278 g of water in a 500 ml Erlenmeyer flask are heated to 70° C. The lipid mixture is stirred into the water and then is dispersed with 35 kHz ultrasonics for 10 minutes. Thereupon the substance is cooled with slight stirring to room temperature. The size of the lipid nano-particles so obtained is about 200 nm. The concentration of the suspension is 7.5% by weight, with the ratio of lipid to surfactant being 1:0.1. The proportion of effective substance in the lipid nano-pellets is 2.65% by weight.

EXAMPLE 15

20.0 g of stearyl alcohol are molten at 70° C. A mixture of 2.0 g of polyethylene glycol sorbitane monooleate (Tween 80) and 0.2 g of Bromazepam are dissolved in the melt. A clear solution is obtained. 178 g of water are placed in a 500 ml Erlenmeyer flask and also are heated to 70° C. The lipid phase is stirred into the water and the substance is then dispersed for 10 minutes using 35 kHz ultrasonics. Next the substance is cooled to room temperature with constant stirring. Thereupon 100 g of ice water are added to the suspension so obtained. The size of the lipid nano-pellet particles is about 800 nm. The concentration of the suspension is 7.4% by weight, with the ratio of lipid to surfactant being 1:0.1. The proportion of effective substance is the lipid nano-pellets is 0.9% by weight.

The principles, preferred embodiments and modes of operation of the present invnetion have been described in the foregoing specification. The invention which is intended to be protected herein, however, is not to be construed as limited to the particular forms disclosed since these are to be regarded as illustrative rather than restrictive. Variations and changes may be made by those skilled in the art without departing from the spirit of the invention.

What is claimed is:

1. An excipient system containing a pharmacologically effective substance for peroral administration characterized in that the excipient system comprises lipid nano-pellets having a particle size of from about 50 to 1000 nm in the form of an aqueous, colloidal suspension, the lipid particles being present in the suspension in a concentration of from about 1 to 20% by weight, said lipid particles consisting of a mixture of at least one lipid and at least one surfactant in a ratio of from about 1:0.1 to 1:2.2, respectively, said particles consisting of from about 5 to 70%.by weight of at least one lipid, from about 0.01 to 70% by weight of at least one surfactant, and from about 0.05 to 25% by weight of a pharmacologically effective substance.

2. The excipient system of claim 1 wherein said lipid nano-pellets have a particles size of from about 80 to 800 nm.

3. The excipient system of claim 1 wherein said at least one lipid and at least one surfactant are present in a ratio of from about 1:0.22 to 1:1.2.

4. The excipient system of claim 1 wherein said lipid at least one lipid and at least one surfactant are present in a ratio of from about 1:1 to 1:0.22.

5. The excipient system of claim 1 wherein said at east one lipid is selected from the group consisting of fatty alcohols of from 12 to 30 carbon atoms and their mono, di and triesters of glycerin and polyvalent alcohols.

6. The excipient system of claim 5 wherein said polyvalent alcohol is selected from the group consisting of ethylene glycol, propylene glycol, mannitol and sorbitol.

7. The excipient system of claim 1 wherein said at least one lipid is a fatty alcohol selected from the group consisting of lauryl alcohol, myristyl alcohol, cetyl alcohol, stearyl alcohol, arachidyl alcohol and behenyl alcohol.

8. The excipient system of claim 1 wherein said at least one lipid is selected from the group consisting of lignoceryl alcohol, ceryl alcohol, cerotyl alcohol and myricyl alcohol.

9. The excipient system of claim 1 wherein said at least one lipid is a mixture of lipids.

10. The excipient system of claim 1 wherein said at least one surfactant comprises a natural bile salt.

11. The excipient system of claim 1 wherein said at least one surfactant is selected from the group consisting of sodium cholate, sodium dehydrocholate, sodium deoxycholate, sodium glycocholate, sodium laurocholate and mixtures thereof.

12. The excipient system of claim 1 wherein said at least one surfactant is selected from the group consisting of salts of sulfo-succinic acid esters, polyoxyethylene sorbitane esters, sorbitane esters, sorbitane ethers, polyoxyethylene fatty alcohol ethers, polyoxyethylene stearic acid esters, mixed condensates of polyoxyethylene ethers with polyoxypropylene ethers, ethoxylated saturated glycerides, partial fatty acid glycerides and polyglycides.

13. The excipient system of claim 1 wherein said at least one surfactant is a mixture of surfactants.

14. The excipient system of claim 1 wherein said lipid particles are present in said suspension in an amount of from about 8 to 15% by weight.

15. The excipient system of claim 14 wherein said lipid particles are present in said suspension in an amount of about 10% by weight.

16. An excipient system containing a pharmacologically effective substance for peroral administration characterized in that the excipient system comprises lipid nano-pellets having a particle size of from about 50 to 1000 nm, said lipid particles consisting of a mixture of at least one lipid and at least one surfactant in a ratio of from about 1:0.1 to 1:2.2, respectively, said particles consisting of from about 5 to 70% by weight of at least one lipid, from about 0.01 to 70% by weight of at least one surfactant, and from about 0.05 to 25% by weight of a pharmacologically effective substance.

17. The excipient system of claim 16 wherein said lipid nano-pellets have a particles size of from about 80 to 800 nm.

18. The excipient system of claim 16 wherein said at least one lipid and at least one surfactant are present in a ratio of from about 1:0.22 to 1:1.2.

19. The excipient system of claim 16 wherein said lipid at least one lipid and at least one surfactant are present in a ratio of from about 1:1 to 1:0.22.

20. The excipient system of claim 16 wherein said at least one lipid is selected from the group consisting of fatty alcohols of from 12 to 30 carbon atoms and their mono, di and triesters of glycerin and polyvalent alcohols.

21. The excipient system of claim 20 wherein said polyvalent alcohol is selected from the group consisting of ethylene glycol, propylene glycol, mannitol and sorbitol.

22. The excipient system of claim 16 wherein said at least one lipid is a fatty alcohol selected from the group consisting of lauryl alcohol, myristyl alcohol, cetyl alcohol, stearyl alcohol, arachidyl alcohol and behenyl alcohol.

23. The excipient system of claim 16 wherein said at least one lipid is selected from the group consisting of lignoceryl alcohol, ceryl alcohol, cerotyl alcohol and myricyl alcohol.

24. The excipient system of claim 16 wherein said at least one lipid is a mixture of lipids.

25. The excipient system of claim 16 wherein said at least one surfactant comprises a natural bile salt.

26. The excipient system of claim 16 wherein said at least one surfactant is selected from the group consisting of sodium cholate, sodium dehydrocholate, sodium deoxycholate, sodium glycocholate, sodium laurocholate and mixtures thereof.

27. The excipient system of claim 16 wherein said at least one surfactant is selected from the group consisting of salts of sulfo-succinic acid esters, polyoxythylene sorbitane esters, sorbitane esters, sorbitane ethers, polyoxyethylene fatty alcohol ethers, polyoxyethylene stearic acid esters, mixed condensates of polyoxyethylene ethers with polyoxypropylene ethers, ethoxylated saturated glycerides, partial fatty acid glycerides and polyglycides.

28. The excipient system of claim 16 wherein said at least one surfactant is a mixture of surfactants.

* * * * *